United States Patent
Miyata et al.

(10) Patent No.: US 9,918,620 B2
(45) Date of Patent: Mar. 20, 2018

(54) OPTICAL TRANSMISSION ELEMENT AND METHOD FOR MANUFACTURING THE SAME

(71) Applicant: OLYMPUS CORPORATION, Tokyo (JP)

(72) Inventors: Akihito Miyata, Akiruno (JP); Yuki Ishikawa, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/168,638

(22) Filed: May 31, 2016

(65) Prior Publication Data

US 2016/0270644 A1 Sep. 22, 2016

Related U.S. Application Data

(63) Continuation of application No. PCT/JP2015/062884, filed on Apr. 28, 2015.

(30) Foreign Application Priority Data

Jul. 22, 2014 (JP) .................................. 2014-148923

(51) Int. Cl.
*G02B 6/00* (2006.01)
*A61B 1/07* (2006.01)
(Continued)

(52) U.S. Cl.
CPC .............. *A61B 1/07* (2013.01); *C03C 25/106* (2013.01); *C03C 25/24* (2013.01); *G02B 6/02395* (2013.01); *G02B 6/06* (2013.01)

(58) Field of Classification Search
CPC ........... A61B 1/07; A61B 1/00; C03C 25/106; C03C 25/24; G02B 6/02395; G02B 6/04; G02B 6/06; G02B 6/44
(Continued)

(56) References Cited

U.S. PATENT DOCUMENTS 5,377,293 A 12/1994 Hatori et al.
6,133,472 A * 10/2000 Nalewajek .............. C07C 43/17
554/225

(Continued)

FOREIGN PATENT DOCUMENTS

JP H02-141440 A 5/1990
JP 2001-502653 A 2/2001
(Continued)

OTHER PUBLICATIONS

Salager, FIRP Booklet #E300-A, "Surfactants Types and Uses", Merida-Venezuela Verson #2 (2002), p. 28.*
(Continued)

*Primary Examiner* — Ellen Kim
(74) *Attorney, Agent, or Firm* — Scully, Scott, Murphy & Presser, P.C.

(57) ABSTRACT

According to an embodiment, there is provided an optical transmission element comprising: a fiber including a core made of a first glass and a cladding made of a second glass and covering an outer periphery of the core; and a covering layer covering an outer periphery of the cladding and including a plurality of nonionic surfactant molecules wherein each of the nonionic surfactant molecules is hydrogen-bonded to the cladding.

11 Claims, 3 Drawing Sheets

(51) Int. Cl.
*C03C 25/24* (2018.01)
*C03C 25/10* (2018.01)
*G02B 6/02* (2006.01)
*G02B 6/06* (2006.01)

(58) Field of Classification Search
USPC .................................. 385/144, 141, 145
See application file for complete search history.

(56) References Cited

U.S. PATENT DOCUMENTS

| | | | | |
|---|---|---|---|---|
| 6,298,189 | B1* | 10/2001 | Szum | C03C 25/1065 385/128 |
| 6,959,022 | B2* | 10/2005 | Sandrock | C03B 37/01426 372/6 |
| 6,966,906 | B2* | 11/2005 | Brown | A61B 1/0051 600/101 |
| 7,447,406 | B2* | 11/2008 | Sutehall | G02B 6/4438 385/109 |
| 8,475,920 | B2* | 7/2013 | Pelizzoni | C08L 23/04 174/110 PM |
| 8,540,627 | B2* | 9/2013 | Feldman | A61B 1/00096 600/130 |
| 2006/0230553 | A1* | 10/2006 | Thullen | C09B 67/0082 8/564 |
| 2008/0304799 | A1* | 12/2008 | Xie | C09J 5/06 385/114 |
| 2008/0305255 | A1* | 12/2008 | Beauvais | G02B 6/08 427/163.2 |
| 2009/0123122 | A1 | 5/2009 | Mukasa | |
| 2013/0330051 | A1* | 12/2013 | Tachibana | G02B 6/4403 385/114 |
| 2013/0343717 | A1 | 12/2013 | Tachibana et al. | |
| 2016/0231505 | A1 | 8/2016 | Miyata et al. | |

FOREIGN PATENT DOCUMENTS

| | | |
|---|---|---|
| JP | 4229890 B2 | 2/2009 |
| JP | 2010-224174 A | 10/2010 |
| JP | 2014-6344 A | 1/2014 |
| WO | 2015/087600 A1 | 6/2015 |

OTHER PUBLICATIONS

International Search Report dated Aug. 11, 2015 issued in PCT/JP2015/062884.
English Abstract of JP 2006-091722 A, dated Apr. 6, 2006.
English Abstract of WO 98/21157, dated May 22, 1998.
International Preliminary Report on Patentability and Written Opinion dated Feb. 2, 2017 received in International Application No. PCT/JP2015/062884.
Chinese Office Action dated Oct. 17, 2017 received in Chinese Patent Application No. 201580003264.5, together with an English-language translation.
European Extended Supplementary Search Report dated Jan. 3, 2018 received in European Patent Application No. 15 82 5051.4.

* cited by examiner

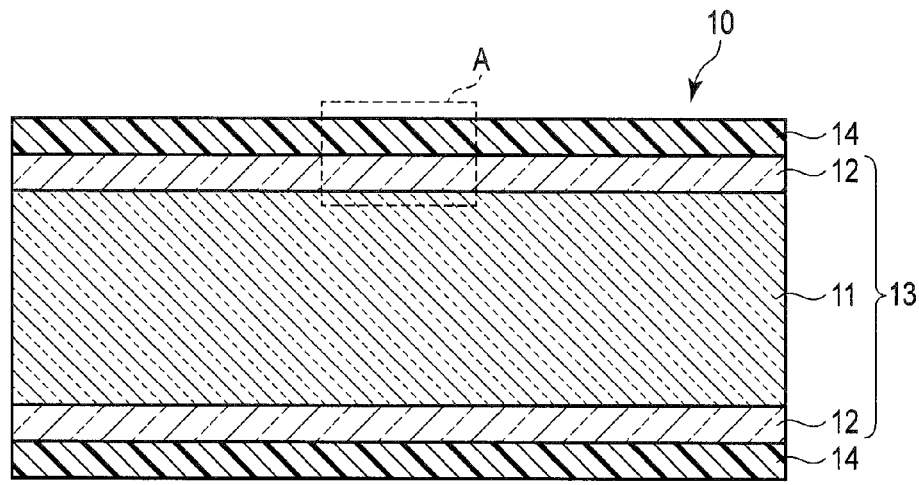
F I G. 1
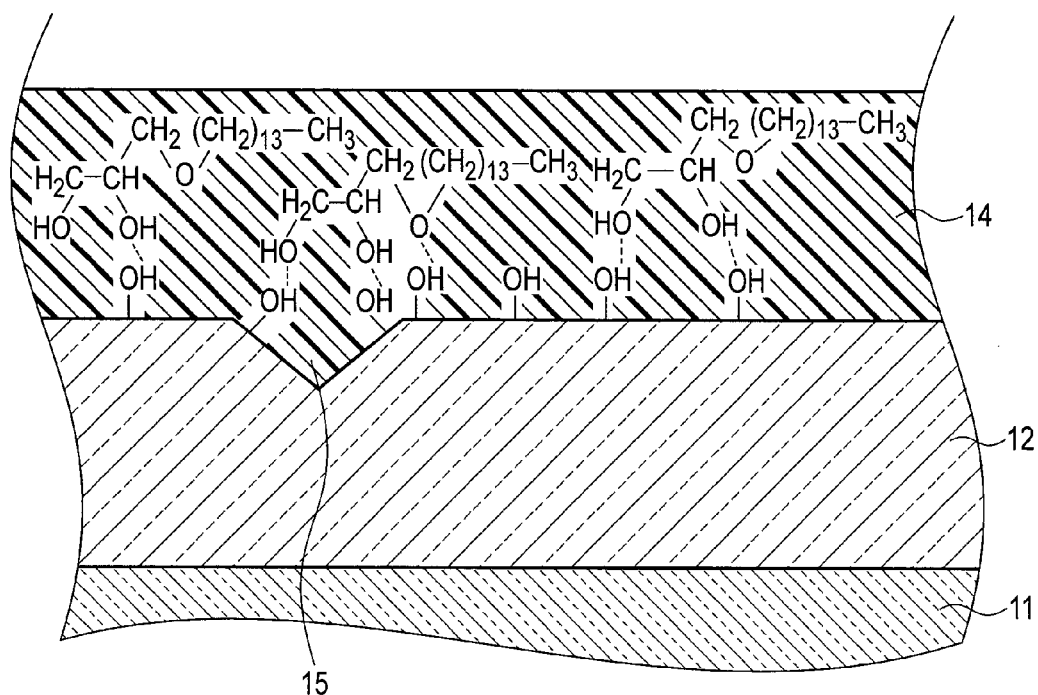
F I G. 2

OPTICAL TRANSMISSION ELEMENT AND METHOD FOR MANUFACTURING THE SAME

CROSS-REFERENCE TO RELATED APPLICATIONS

This application is a Continuation Application of PCT Application No. PCT/JP2015/062884, filed Apr. 28, 2015 and based upon and claiming the benefit of priority from Japanese Patent Application No. 2014-148923, filed Jul. 22, 2014, the entire contents of all of which are incorporated herein by reference.

BACKGROUND OF THE INVENTION

1. Field of the Invention

The present invention relates to an optical transmission element, an image guide or a light guide which includes a plurality of the optical transmission elements, an endoscope including at least one of the image guide and the light guide, and a method for manufacturing the optical transmission element.

2. Description of the Related Art

In a conventional endoscope, a glass optical fiber is passed through an insertion portion of the endoscope in order to secure brightness during observation. Such an optical fiber is used to transmit illumination light toward a tip part from a light source.

The optical fiber has excellent transmissivity and light distribution properties. However, the optical fiber has high hardness and low flexibility in terms of physical properties. Since the tip part of the endoscope is repeatedly severely bent, the optical fiber is disadvantageously apt to break at the tip part. Since the endoscope is densely filled with the optical fibers, the optical fibers suffer from frictional contact also in portions other than the tip part, which disadvantageously causes the optical fibers to break. If the optical fiber in the endoscope breaks, a transmitted light amount is decreased, which causes deterioration in the observation performance of the endoscope.

An optical transmission element as an optical fiber for solving such a problem is disclosed in Japanese Patent No. 4229890. In the optical transmission element, a covering layer including a fluorine-substituted alkyl group-containing organic silicon compound (hereinafter, a fluorinated alkylsilane layer) is formed on the outer periphery of a fiber.

BRIEF SUMMARY OF THE INVENTION

According to one aspect of the present invention, there is provided an optical transmission element comprising:
a fiber including a core made of a first glass and a cladding made of a second glass and covering an outer periphery of the core; and
a covering layer covering an outer periphery of the cladding and including a plurality of nonionic surfactant molecules wherein each of the nonionic surfactant molecules is hydrogen-bonded to the cladding.

BRIEF DESCRIPTION OF THE SEVERAL VIEWS OF THE DRAWING

FIG. 1 is an axial cross-sectional view of an optical transmission element according to an embodiment.

FIG. 2 is an axial cross-sectional view of an optical transmission element according to an embodiment, which represents a magnified view of region A surrounded with a dashed line in FIG. 1.

DETAILED DESCRIPTION OF THE INVENTION

Figure 3:
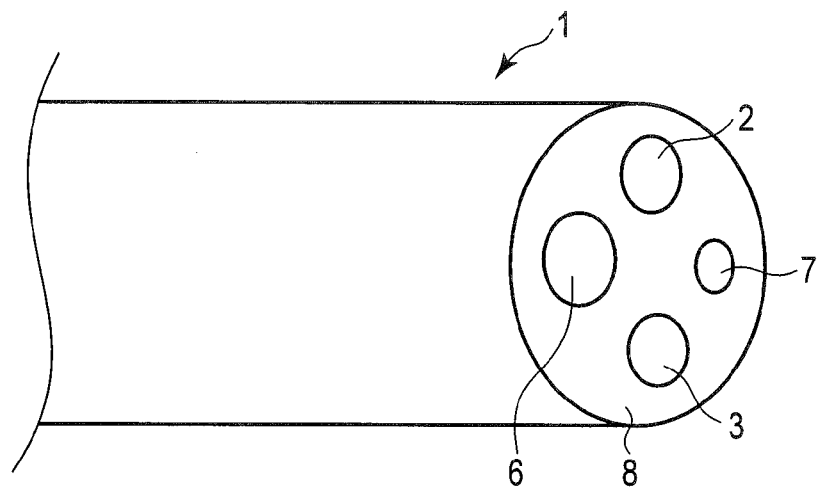
FIG. 3 shows a tip part of an endoscope according to an embodiment.

A first embodiment of the present invention relates to an optical transmission element. FIG. 1 shows an axial cross-sectional view of an optical transmission element.

The optical transmission element is one used as a light waveguide for propagating a light wave, a signal, an image or the like. The optical transmission element includes, for example, an optical fiber, a light guide, an optical fiber sensor or the like. The optical transmission element may have a circular or rectangular cross-section, and the cross-section is not particularly limited.

As shown in FIG. 1, an optical transmission element 10 of the present invention includes a fiber 13 and a covering layer 14.

The fiber 13 mainly transmits light in the optical transmission element 10. The fiber 13 includes a core 11 formed in a cylindrical shape and a cladding 12 covering the outer periphery of the core 11. Both the core 11 and the cladding 12 are made of glass. Preferably, such glass has high optical transparency. Furthermore, a first glass constituting the core 11 preferably has a higher refractive index than that of a second glass constituting the cladding 12. As the first glass and the second glass, silica glass containing an additive can be used, for example.

The covering layer 14 mainly protects the fiber 13 and adjusts the adhesiveness between a plurality of optical transmission elements 10 when the optical transmission elements 10 are bundled. The covering layer 14 covers the outer periphery of the cladding 12. The thickness of the covering layer 14 is not particularly limited. The thickness may be 1 nm to 100 nm, and is, for example, about 10 nm. When the covering layer 14 is too thin, the covering layer 14 cannot sufficiently achieve the role of protecting the fiber. On the other hand, when the covering layer 14 is too thick, the ratio of the cross-sectional area of the fiber 13 to the cross-sectional area of the optical transmission element is decreased, which may cause a decrease in the transmitting efficiency of light.

The covering layer 14 includes a plurality of nonionic surfactant molecules. The covering layer 14 is typically a monomolecular layer. Each of the nonionic surfactant molecules is bonded to the cladding 12 via a hydrogen bond.

A nonionic surfactant is a surfactant having a hydrophilic group which is not ionized when the surfactant is dissolved in water. The nonionic surfactant is classified into an ether type, an ester type, and other types. The nonionic surfactant used in the present embodiment preferably has a hydroxyl group as the hydrophilic group. For example, the hydroxyl group is hydrogen-bonded to the cladding to form a covering layer including the nonionic surfactant molecules on the outer periphery of the cladding.

FIG. 2 shows an axial cross-sectional view of an optical transmission element according to an embodiment, which represents a magnified view of region A surrounded with a dashed line in FIG. 1. In FIG. 2, the case where 1-O-tetradecylglycerin is used as the nonionic surfactant molecule is shown. As shown in FIG. 2, the hydroxyl groups in the nonionic surfactant molecules are bonded to the cladding 12 via hydrogen bonds to form the covering layer 14.

By forming such a covering layer 14, a frictional force acting on the contact surface between the optical transmission elements can be reduced. Because of this, the durability, abrasion resistance, and lubricity of the fiber 13 can be improved.

As shown in FIG. 2, a micro crack 15 may exist on the outer periphery of the cladding 12. The nonionic surfactant molecule can cover such a crack 15, which can prevent the breaking of the fiber 13 caused by the crack 15 to improve the durability of the optical transmission element.

Each of the nonionic surfactant molecules preferably has two or more hydroxyl groups. As the number of the hydroxyl groups per molecule is increased, each of the molecules is more strongly bonded to the outer periphery of the cladding 12, and thereby it is harder for the covering layer 14 to be peeled off. Therefore, durability and abrasion resistance can be further improved. The number of the hydroxyl groups is preferably 12 or less, for example. When the number of the hydroxyl groups is excessively increased, the number of the hydroxyl groups which cannot be hydrogen-bonded to the cladding 12 is increased. As a result, such hydroxyl groups of the surfactant interact with each other on the outer periphery of the cladding 12, which may cause deterioration in the lubricity of the fiber 13. The number of the hydroxyl groups is more preferably 3 to 10 per molecule.

When the number of the hydroxyl groups per molecule is 2 or more, each of two or more hydroxyl groups can be bonded to the cladding so that it straddles the micro cracks 15 which exist on the outer periphery of the cladding 12, as shown in FIG. 2. Thereby, the effect of covering the cracks is considered to be further improved.

The nonionic surfactant molecule typically has at least one of an ether bond and an ester bond. An oxygen atom included in at least one of the ether bond and the ester bond, and a hydroxyl group of the cladding may be bonded via a hydrogen bond. The nonionic surfactant molecule preferably has any selected from hydroxyl groups, ether bonds and ester bonds in a total number of two or more in the molecule.

The nonionic surfactant molecule may have a hydroxyl group which is not hydrogen-bonded to the hydroxyl group of the cladding. Dehydration condensation may occur between such a hydroxyl group and a hydroxyl group of the other adjacent nonionic surfactant molecule or a hydroxyl group which exists on the surface of the cladding.

The hydrophobic group of the nonionic surfactant molecule preferably has a hydrocarbon chain having 8 carbon atoms or more. The hydrocarbon chain of the hydrophobic group may be a saturated hydrocarbon chain, or an unsaturated hydrocarbon chain. Herein, when the hydrophilic group and hydrophobic group of the nonionic surfactant molecule are separated by the ester bond, the carbon of the ester bond is not regarded as the carbon of the hydrophobic group.

When the number of the carbon atoms of the hydrophobic group is excessively decreased, the optical transmission element may have insufficient durability, abrasion resistance, and lubricity. When the number of the carbon atoms is excessively increased, the area of the hydrocarbon chain covering the outer periphery of the cladding 12 is increased. As a result, an adhesive and a reaction group are relatively decreased, which may cause a decrease in adhesive strength.

As the nonionic surfactant, for example, polyoxyalkylene ether, sorbitan fatty acid ester, polyoxyethylene sorbitol fatty acid ester, glyceryl ether, glycerin fatty acid ester, polyoxyethylene fatty acid ester, polyoxyethylene hardened castor oil or the like can be used. More preferable examples thereof include polyoxyethylene sorbitan monooleate (20E.O.), decaglyceryl monostearate, and monooleyl glyceryl ether.

In a preferable embodiment, the optical transmission element includes a lead-free fiber which does not contain lead. Since detrimental substances such as lead are strictly regulated in recent years, the requirement of the lead-free fiber has been increased. However, the lead-free fiber has higher hardness and lower flexibility than those of the lead-containing fiber, which disadvantageously has low durability.

However, the fiber is covered with the covering layer including the nonionic surfactant molecules according to the present embodiment, and thereby even the lead-free fiber can have sufficient durability, abrasion resistance, and lubricity.

The covering layer can be formed by applying a treatment liquid containing a nonionic surfactant and water to the outer periphery of the cladding. The treatment liquid may contain other ingredients, but it may contain only a nonionic surfactant and water. The ratio of the nonionic surfactant in the treatment liquid is 0.01 to 20% by volume, for example, and preferably 0.2 to 10% by volume. When the ratio is within the range, the nonionic surfactant molecules constitute the covering layer at a suitable density, and thereby sufficient durability, abrasion resistance, and lubricity are obtained, which makes it hard for the covering layer to be peeled off. When the ratio is excessively increased, the nonionic surfactant molecules form micelle, which makes it impossible to obtain a homogeneous covering layer. This is considered to deteriorate durability, abrasion resistance, and lubricity.

The method for applying the treatment liquid is not particularly limited. For example, the treatment liquid can be applied by a die coat method, a spray method, a dipping method, or a shower method. The die coat method refers to a method of passing a fiber through a die while supplying a coating liquid to the die to form a covering layer on the surface of the fiber. The spray method refers to a method of spraying a coating liquid on the surface of a fiber. The dipping method refers to a method of immersing a fiber into a coating liquid. The shower method refers to a method of passing a fiber through a shower of a coating liquid.

A second embodiment of the present invention relates to an image guide, a light guide, and an endoscope using them. An example of a tip part of an endoscope 1 according to an embodiment is shown in FIG. 3. In the endoscope 1, an image guide 2 and a light guide 3 are inserted into a tip element 8. A forceps port 6 used for inserting and removing a treatment tool for collecting a tissue or excising a lesion, and a nozzle 7 for sending out water for cleaning lens or air for swelling a body cavity also are provided in the tip element 8.

Figure 4:
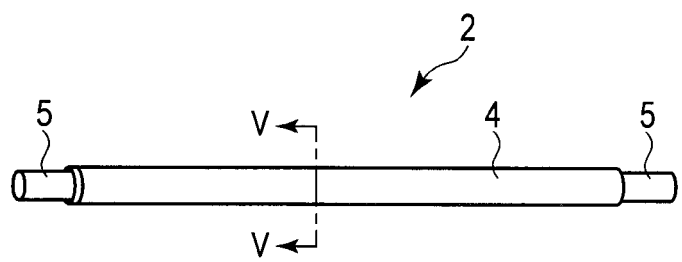
FIG. 4 shows an image guide according to an embodiment.
Figure 5:
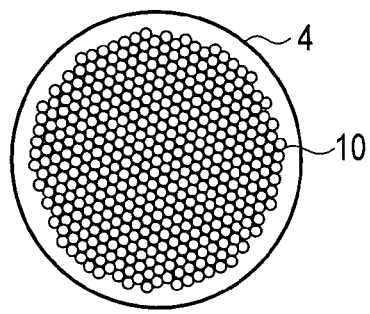
FIG. 5 is a cross-sectional view of the image guide taken along line V-V in FIG. 4.

In the image guide 2 and the light guide 3, a plurality of optical transmission elements according to the first embodiment are bundled. An example of the image guide 2 is shown in FIG. 4. FIG. 5 shows a cross-sectional view of the image guide 2 taken along line V-V in FIG. 4.

As shown in FIG. 5, the image guide 2 has a configuration in which a plurality of optical transmission elements 10 is bundled and the bundle is stored in a jacket tube 4.

In one embodiment, a solid lubricant may be applied to the outer periphery of each of the optical transmission elements 10. By applying the solid lubricant, lubricity can be imparted to the optical transmission element, and thereby a frictional force acting on the contact surface between the optical transmission elements can be further reduced.

Examples of the solid lubricant include talc, boron nitride, molybdenum disulfide, a fluoride resin such as ethylene fluoride, polyacetal, and carbon graphite.

In another embodiment, the solid lubricant may not be applied to each of the optical transmission elements 10. That is, a covering layer 14 may exist on the outermost periphery of the optical transmission element 10. According to the first embodiment, the optical transmission element having the covering layer 14 including a nonionic surfactant has sufficient durability, abrasion resistance, and lubricity, and thus desired performance can be obtained even if the solid lubricant is not applied thereto.

As shown in FIG. 4, the image guide 2 comprises a ferrule 5 at both the ends. The image guide 2 is incorporated into an endoscope by inserting the ferrule 5 into a through hole provided in the tip element 8 as shown in FIG. 3. Herein, the image guide 2 has been described as an example, but the light guide 3 also has the same configuration.

The optical transmission element according to the embodiment can achieve a more excellent effect than that of a conventional optical transmission element. The effect will be described below.

Figure 6:
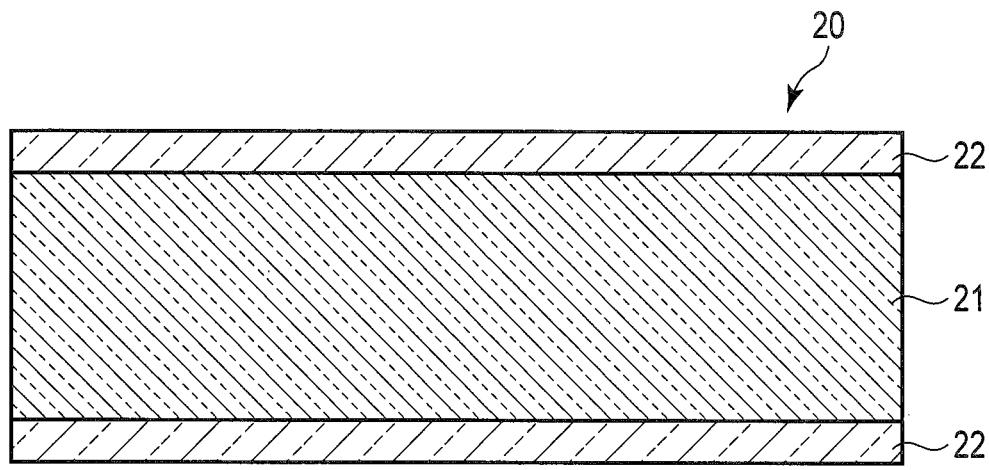
FIG. 6 is an axial cross-sectional view of a conventional optical transmission element which is not covered.
Figure 7:
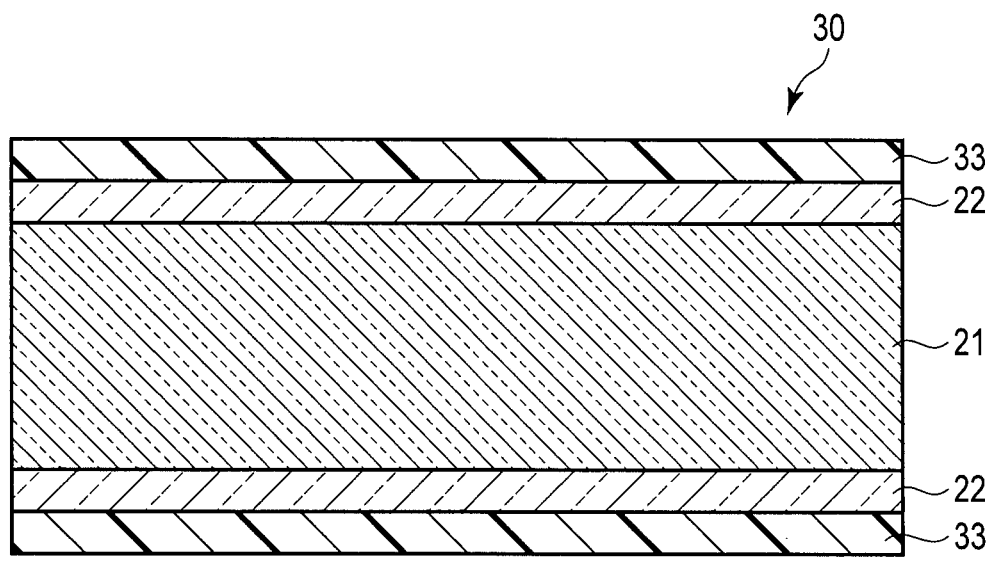
FIG. 7 is an axial cross-sectional view of a conventional optical transmission element which is covered with a fluorinated alkylsilane layer.

An example of a conventional optical transmission element is shown in FIG. 6 and FIG. 7. FIG. 6 shows an axial cross-sectional view of an optical transmission element 20 including a core 21 and a cladding 22 and having no covering layer. FIG. 7 shows an axial cross-sectional view of an optical transmission element 30 which includes a core 21 and a cladding 22, and has a covering layer 33 including a fluorinated alkylsilane layer.

An optical transmission element 20 having no covering layer as shown in FIG. 6 has poor durability, abrasion resistance, and lubricity. In particular, a fiber made of lead-free glass has higher hardness and lower flexibility in terms of physical properties than those of a lead-containing fiber. Therefore, when the tip part of the endoscope densely filled with the fiber is repeatedly severely bent, it causes the fiber to break in many cases. This leads to deterioration in the observation performance of the endoscope.

An optical transmission element having a fluorinated alkylsilane layer 33 as shown in FIG. 7 has excellent durability, abrasion resistance, and lubricity due to the existence of the covering layer including fluorinated alkylsilane. This can reduce the breaking and deterioration to such an extent that sufficient observation performance is obtained. However, a fluorinated alkyl group in the covering layer is exposed from the surface of the optical transmission element, which disadvantageously deteriorates the adhesiveness between the plurality of optical transmission elements when the optical transmission elements are bundled.

When the image guide or light guide used for the endoscope is manufactured, generally, the plurality of optical transmission elements are bundled, and the bundle is stored in the jacket tube. Then, the end parts of the bundle are polished. As a result, the end faces of each of the optical transmission elements are polished to improve optical transparency and align the positions of the end faces of the plurality of optical transmission elements. However, the adhesiveness between the optical transmission elements having the fluorinated alkylsilane layer is low. When the adhesiveness between the optical transmission elements is low, the fixation of each of the optical transmission elements is insufficient, which makes the polishing difficult. In this case, the edge of the end faces of each optical transmission element is scraped, or some of the end faces of the optical transmission elements are buried. As a result, there is a problem that the observation performance of the endoscope is deteriorated.

On the other hand, the optical transmission element according to the present invention has excellent durability, abrasion resistance and lubricity, and high adhesiveness. This enables suitable polishing. By using such optical transmission elements, the image guide and light guide having excellent durability and optical transparency can be provided. Furthermore, by using such image guide and light guide, an endoscope having excellent observation performance can be provided.

EXAMPLES

An optical transmission element according to an embodiment was manufactured, and the durability and polishing state of the optical transmission element were evaluated.

Example 1

<Preparation of Treatment Liquid>

A nonionic surfactant was dissolved in water to prepare a treatment liquid. As the nonionic surfactant, polyoxyethylene sorbitan monooleate (20E.O.) represented by the formula 1 was used. The ratio of the nonionic surfactant in the treatment liquid was 1% by volume.

[Chemical Formula 1]

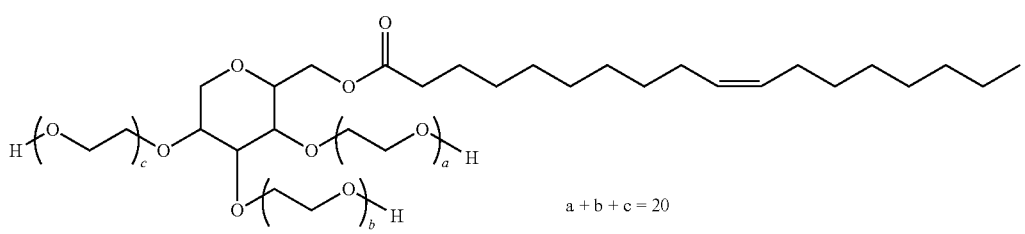

Formula 1

$a + b + c = 20$

<Production of Optical Transmission Element>

An optical transmission element was produced using a fiber which is free of lead. First, a fiber was immersed into the treatment liquid prepared as described above for 10 seconds. Subsequently, the fiber was removed from the treatment liquid, and dried. In this way, an optical transmission element in which a covering layer was formed on the outer periphery of the fiber was obtained.

<Production of Bundle>

The plurality of optical transmission elements produced above were collectively stored in a silicone tube. Subsequently, each end of the optical transmission elements was inserted into a ferrule, and then sealed with an adhesive, followed by cutting and polishing. In this way, a bundle of Example 1 was obtained.

Example 2

A bundle was produced in the same manner as in Example 1 except that decaglyceryl monostearate represented by the formula 2 was used as a nonionic surfactant.

[Chemical Formula 2]

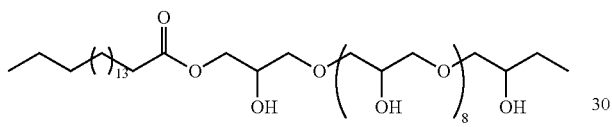

Formula 2

Example 3

A bundle was produced in the same manner as in Example 1 except that monooleyl glyceryl ether represented by the formula 3 was used as a nonionic surfactant.

[Chemical Formula 3]

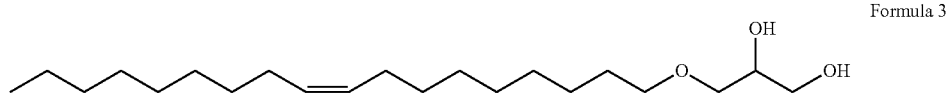

Formula 3

Comparative Example 1

A bundle was produced in the same manner as in Example 1 except that a fluorine-substituted alkyl group-containing organic silicon compound was used in place of a nonionic surfactant, and a treatment liquid was prepared using a fluorine-based solvent in place of water. The ratio of the fluorine-substituted alkyl group-containing organic silicon compound in the treatment liquid was 1% by volume.

Comparative Example 2

A bundle was produced in the same manner as in Example 1 except that myristic acid represented by the formula 4 was used in place of a nonionic surfactant, and a treatment liquid was prepared using ethanol in place of water. The ratio of myristic acid in the treatment liquid was 5% by volume.

[Chemical Formula 4]

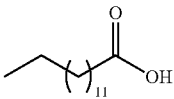

Formula 4

Comparative Example 3

A bundle was produced in the same manner as in Example 1 except that palmitic acid represented by the formula 5 was used in place of a nonionic surfactant, and a treatment liquid was prepared using ethanol in place of water. The ratio of palmitic acid in the treatment liquid was 5% by volume.

[Chemical Formula 5]

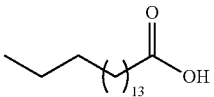

Formula 5

Comparative Example 4

A bundle was produced in the same manner as in Example 1 except that fluorine-modified silicone oil (100% by volume) was used as a treatment liquid.

[Chemical Formula 6]

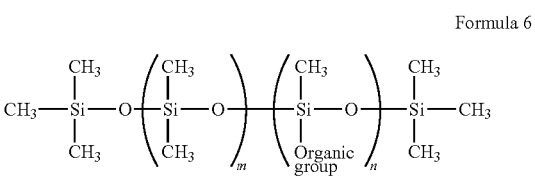

Formula 6

Comparative Example 5

A bundle was produced in the same manner as in Example 1 using a fiber having no covering layer.

<Evaluation of Durability>

Durability was evaluated for each of the bundles of Examples 1 to 3 and Comparative Examples 1 to 5.

For evaluation, a test was carried out by simulating a load applied when a tip part of an endoscope was repeatedly bent to manipulate the endoscope. Specifically, after a higher load than that in the case of manipulating the endoscope was repeatedly applied to each bundle a given number of times, the number of the broken optical transmission elements was counted. From the result, a breaking rate (%) was calculated according to the following formula:

breaking rate (%)=(number of optical transmission elements broken after test)/(total number of optical transmission elements)×100

The evaluation results on the durability of the bundles of Examples 1 to 3 and Comparative Examples 1 to 5 are shown in Table 1. In Table 1, a bundle having a breaking rate of less than 10% was defined as "⊚ (very good)". A bundle having a breaking rate of 10% or more and less than 60% was defined as "○ (good)". A bundle having a breaking rate of 60% or more was defined as "x (poor)". Table 1 also shows the number of hydroxyl groups of the nonionic surfactant used in each of Examples.

<Evaluation of Polishing State>

Furthermore, the end faces of the bundles of Examples 1 to 3 and Comparative Examples 1 to 5 were polished, and the states of the end faces of the polished bundles were observed. The results are shown in Table 1. In Table 1, a bundle having a usable level for the observation performance of the endoscope was evaluated as "○ (good)", and a bundle having an unusable level for the observation performance of the endoscope was evaluated as "x poor".

TABLE 1

|  | Component name | Substance name | Number of hydroxyl groups of active ingredient | Ratio of active ingredient in treatment liquid (% by volume) | Durability | Polishing state |
|---|---|---|---|---|---|---|
| Example 1 | Active ingredient | Polyoxyethylene sorbitan monooleate (20E.O.) | 3 | 1 | ○ | ○ |
|  | Solvent | Water |  |  |  |  |
| Example 2 | Active ingredient | Decaglyceryl monostearate | 10 | 1 | ○ | ○ |
|  | Solvent | Water |  |  |  |  |
| Example 3 | Active ingredient | Monooleyl glyceryl ether | 2 | 1 | ○ | ○ |
|  | Solvent | Water |  |  |  |  |
| Comparative Example 1 | Active ingredient | Fluorine-substituted alkyl group-containing organic silicon compound | 3 | 1 | ⊚ | X |
|  | Solvent | Fluorine-based solvent |  |  |  |  |
| Comparative Example 2 | Active ingredient | Myristic acid | 1 | 5 | X | ○ |
|  | Solvent | Ethanol |  |  |  |  |
| Comparative Example 3 | Active ingredient | Palmitic acid | 1 | 5 | X | ○ |
|  | Solvent | Ethanol |  |  |  |  |
| Comparative Example 4 | Active ingredient | Fluorine-modified silicone oil | 0 | 100 | X | ○ |
|  | Solvent | Not applicable |  |  |  |  |
| Comparative Example 5 | Active ingredient | Not applicable (No coat) | — | — | X | ○ |
|  | Solvent | Water |  |  |  |  |

From the results shown in Table 1, the following is found. Comparative example 1 had highly excellent durability, but it had a poor polishing state, and was not suitable for use. Comparative Examples 2, 3, and 4 using no nonionic surfactant as the covering layer had low durability, and were not suitable for use. Comparative Example 5 including no covering layer had remarkably low durability.

On the other hand, it was shown that all the Examples using the nonionic surfactants had excellent durability and polishing properties.

What is claimed is:

1. An optical transmission element comprising:
   a fiber including a core made of a first glass and a cladding made of a second glass and covering an outer periphery of the core; and
   a covering layer covering an outer periphery of the cladding, the covering layer formed by application of a treatment liquid consisting of a nonionic surfactant and water to the outer periphery of the cladding wherein each molecule of the nonionic surfactant is hydrogen-bonded to the cladding.

2. The optical transmission element according to claim 1, wherein each molecule of the nonionic surfactant has a hydroxyl group.

3. The optical transmission element according to claim 2, wherein each molecule of the nonionic surfactant has two or more hydroxyl groups.

4. The optical transmission element according to claim 2, wherein each molecule of the nonionic surfactant has at least one of an ether bond and an ester bond in the molecule, and the total number of the hydroxyl group, ether bond, and ester bond is 2 or more.

5. The optical transmission element according to claim 1, wherein each molecule of the nonionic surfactant has a hydrocarbon chain having 8 or more carbon atoms.

6. The optical transmission element according to claim 1, wherein the fiber is free of lead.

7. The optical transmission element according to claim 1, further comprising a solid lubricant applied to an outer periphery of the covering layer.

8. An image guide wherein a plurality of the optical transmission elements according to claim 1 are bundled.

9. A light guide wherein a plurality of the optical transmission elements according to claim 1 are bundled.

10. An endoscope comprising at least one of the image guide according to claim 8 and the light guide according to claim 9.

11. A method for manufacturing an optical transmission element, comprising:
applying a treatment liquid consisting of a nonionic surfactant and water to an outer periphery of a fiber including a core made of first glass and a cladding made of second glass and covering an outer periphery of the core,
wherein a ratio of the nonionic surfactant in the treatment liquid is 0.01 to 20% by volume.

* * * * *